United States Patent [19]

Van Boom et al.

[11] Patent Number: 4,503,233
[45] Date of Patent: Mar. 5, 1985

[54] PHOSPHORYLATING AGENT AND PROCESS FOR THE PHOSPHORYLATION OF ORGANIC HYDROXYL COMPOUNDS

[75] Inventors: Jacobus H. Van Boom, Voorschoten; Gijsbert A. Van Den Marel, Warmond; Constant A. A. Van Boeckel, Oss, all of Netherlands

[73] Assignee: Internationale Octrooi Maatschappij "Octropa" BV, Rotterdam, Netherlands

[21] Appl. No.: 376,510

[22] Filed: May 10, 1982

[30] Foreign Application Priority Data

May 12, 1981 [NL] Netherlands .......................... 8102323

[51] Int. Cl.$^3$ ................................................ C07F 9/65
[52] U.S. Cl. ...................................... 548/114; 536/26; 536/27; 536/28
[58] Field of Search .......................... 548/114; 544/132

[56] References Cited

FOREIGN PATENT DOCUMENTS 0064796 11/1982 European Pat. Off. ............ 548/114

OTHER PUBLICATIONS

Marel et al., Tetrahedron Letters, 22, (39), pp. 3887–3890, (Sep. 1981).
Chemical Abstracts, 96:85909h, (1982).
Chemical Abstracts, 88:23374f, (1978).
Chemical Abstracts, 79:32063v, (1973).
Chemical Abstracts 92:181088c, (1980).
Marel et al., Tetrahedron Letters, 22, (15), 1463–1466, (1981).
Rooij et al., Journ. Royal Netherlands Chem. Soc., 98/11, (1979).
Chattopadhyaya et al., Tetrahedron Letters, No. 52, pp. 5059–5062.
Reese et al., Tetrahedron Letters, vol. 21, pp. 2265–2268, (1980).
Katagiri et al., Journ. Amer. Chem. Soc., 97, (25), 12-10-75.

*Primary Examiner*—Ethel G. Love
*Attorney, Agent, or Firm*—Cushman, Darby & Cushman

[57] ABSTRACT

The invention relates to new phosphorylating agents, a process for producing said compounds and their use in a process for the phosphorylation of organic hydroxyl compounds to obtain intermediate products useful for the production of polynucleotides. The phosphorylation is achieved without side reactions at the purine- or pyrimidine bases.

2 Claims, 16 Drawing Figures

PHOSPHORYLATING AGENT AND PROCESS FOR THE PHOSPHORYLATION OF ORGANIC HYDROXYL COMPOUNDS

The present invention relates to phosphoric acid derivatives suitable for use as phosphorylating agents. The invention also relates to a process of phosphorylating organic hydroxyl compounds and to phosphotriester intermediates suitable for use in the synthesis of polynucleotides, which include nucleic acids.

Nucleic acids can be subdivided into two types:

(a) the deoxyribonucleic acids (DNA), which form the material basis for the genetic information of all organisms; and (b) the ribonucleic acids (RNA), which are known as messenger, transfer and ribosomal RNA.

DNA- and RNA-fragments are short-length oligonucleotides or polynucleotides, consisting of chains of nucleotides which are interconnected by a phosphoric acid diester compound between the 3'-position of one nucleoside and the 5'-position of the other nucleoside.

A frequently used method for the preparation of polynucleotides is the so-called phosphotriester approach as described in "Tetrahedron" 34, 3143–3179 (1978).

A crucial step in the synthesis of polynucleotides via the phosphotriester approach is phosphorylation. Hence the particular efforts being made in research in finding new agents with a phosphorylating action that is not only effective and efficient, but at the same time selective. For the synthesis of oligonucleotides and nucleic acids it is particularly important to find phosphorylating agents with which nucleoside-phosphotriester intermediaries can be obtained without the occurrence, during their formation, of side reactions at the bases guanine, adenine, cytosine, thymine or uracil, which are or are not provided with a protective group. In addition, the so formed nucleoside-phosphotriester intermediaries should be suitable for the formation of 3'-5'-internucleotide phosphodiester compounds, so as to allow the synthesis of polynucleotides.

Various formulas or reactions relevant to the invention are shown in FIGS. 1–16.

Figure 1:
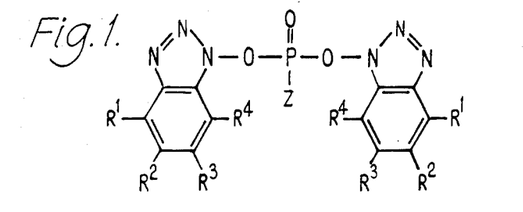

The phosphoric acid derivatives according to the invention that can be used as phosphorylating agents satisfy FIG. 1, in which $R^1$, $R^2$, $R^3$, and $R^4$ are $C_{1-4}$ alkyl groups and/or hydrogen and in which Z represents either an $OR^5$-group in which $R^5$ is an alkyl or aryl group, or a primary or secondary amine.

Figure 6:
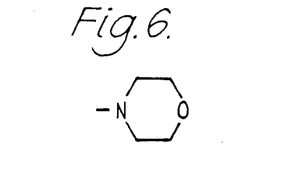

Preferably, $R^1$, $R^2$, $R^3$ and $R^4$ are hydrogen atoms and Z is a morpholino group with formula 6 or an $OR^5$-group in which $R^5$ is a 2-halophenyl, a 4-haloophenyl or a 2-halo-4-alkylphenyl group.

Figure 2:
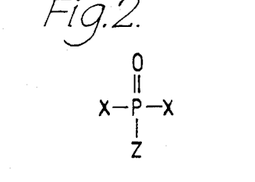
Figure 3:
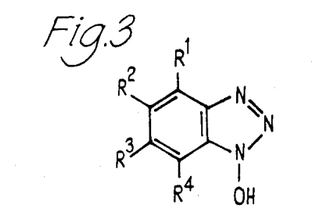

The phosphorylating agents according to the invention can be prepared by reacting a compound with FIG. 2, in which X is a halogen atom and Z has the same meaning as in FIG. 1, with a compound with FIG. 3, in which $R^1$, $R^2$, $R^3$ and $R^4$ have the same meaning as in FIG. 1.

In FIG. 2, X preferably is a chlorine atom and $R^1$, $R^2$, $R^3$ and $R^4$ preferably are hydrogen atoms.

The reaction is carried out in the presence of an inert organic solvent such as tetrahydrofuran (THF), preferably in the presence of a teriary amine base such as pyridine. The phosphorylating agents with FIG. 1 can be used for the phosphorylation of hydroxyl compounds such as a monosaccharide or a derivative thereof, a nucleoside, a nucleotide or a polynucleotide.

The nucleosides or 3'-5'-polynucleotides subjected to phosphorylation preferably have a protected 3'-hydroxyl group or a protected 5'-hydroxyl group and possibly other reactive groups protected by protective groups. These polynucleotides can be protected or non-protected DNA- or RNA-fragments.

Figure 4:
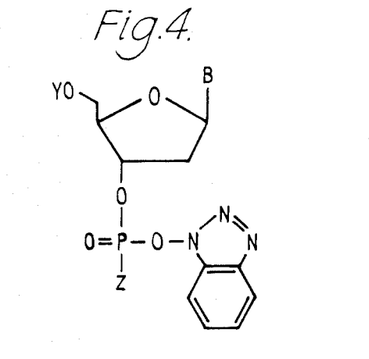

The simplest conceivable monomeric intermediate derived from deoxyribose satisfies FIG. 4, in which B is a protected or non-protected purine or pyrimidine base, Y is a group protecting a hydroxyl group, and Z has the same meaning as in FIG. 1. For example, Y can be a t-butyldimethylsilyl group or a dimethoxytrityl group. B can be thymine (T), N(6)-Benzoyladenine ($A^{Bz}$), N(4)-Anisoylcytosine ($C^{An}$) or N(2)-diphenylacetylguanosine ($G^{DPA}$).

Figure 5:
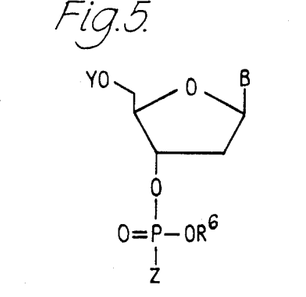

The intermediates with FIG. 4 can be converted with hydroxyl compounds having formula $R^6OH$, in which $R^6$, for example, is an alkylhalogenide-, alkylcyanide-, 4-phenylethyl-, 5-chloro-8-quinol group and preferably represents those groups that are illustrated in the Table, resulting in compounds with FIG. 5 in which Y and B have the same meaning as in FIG. 4.

The conversion is preferably performed in the presence of a tertiary amine base and especially in the presence of pyridine or N-methylimidazole. The latter compound appeared to increase the phosphorylation rate approximately four times more than is effected by pyridine.

The invention further relates to a process of preparing di- and polynucleotides, in which 3'-5'-internucleotide phosphotriester compounds are obtained, using the previously mentioned phosphorylated intermediates with FIG. 4.

In the preparation of dimers or dinucleotides, such as e.g. fully protected GpT, it was found that the synthesis thereof took place without any appreciable side reaction or discoloration of the reaction mixture. This is most surprising since when using phosphorylating agents other than the present phosphoric acid derivatives, in many experiments regarding the synthesis of guanine containing DNA-fragments it was invariably established, depending on the phosphotriester method applied, that by-products had been formed and that discoloration of the reaction mixture had occurred. (See for example:

J. F. M. de Rooij, G. Wille-Hazeleger, J. Serdijn et al, Recl.Trav.Chim.Pays-Bas, 98, 53 (1979);

J. Stawinsky, T. Hozumi, S. A. Narang et al, Nucleic Acids Res., 4, 353 (1977);

J. B. Chattopadhyaya and C. B. Reese, Tetrahydron Letters, 5059 (1979);

C. B. Reese and A. Ubasawa, Tetrahydrol Letters, 2265 (1980)).

The invention is particularly directed to polynucleotides obtained by means of the aforementioned process, in which preference is given to protected RNA- and DNA-fragments.

The process referred to herein is preferably carried out in the presence of a solid carrier, such as cellulose, polystyrene, polyacrylamide or silica, which has preferably been functionalised as illustrated in the Examples. The invention will now be further illustrated by means of the following Examples.

EXAMPLE I

Figure 7:
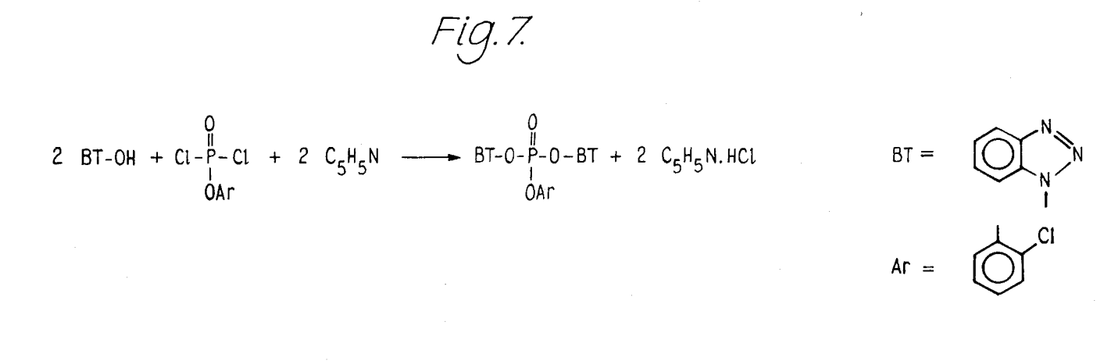

Preparation of 2-chlorophenylphosphorodi-1-hydroxy benzotriazolidate 1 mmol 2-chlorophenylphosphorodichloridate (FIG. 2, in which X is Cl and $R^5=2\text{-ClC}_6H_4$) was added to a stirred solution of 2 mmol 1-hydroxy benzotriazole (HOBT) in 5 ml dry tetrahydrofuran (THF) in the presence of 2 mmol pyridine. The reaction mixture was kept at 20° C. for 1 hour. From the amount of pyridinium-HCl-salt formed it could be concluded that the reaction was complete. $^{31}$P-NMR-analysis showed a signal at $\delta=8.31$ ppm with respect to external phosphoric acid (i.e. phosphoric acid in a separate tube). The reaction equation is given in FIG. 7.

EXMAPLE II

Phosphorylation of 5'-t-butyldimethylsilylthymidine with 2-chlorophenylphosphorodi-1-hydroxy benzotriazolidate to a phosphotriester intermediate 1 mmol 5'-t-butyldimethylsilylthymidine was added to a stirred solution of 1.1 mmol 2-chlorophenylphosphorodi-1-hydroxy benzotriazolidate in 5 ml THF. After 30 minutes at 20° C., TLC-analysis (CHCl$_3$:MeOH, 92:8, v/v) indicated that the starting product had entirely been converted into the intermediate desired.

Hydrolysis of the formed intermediate having FIG. 4, in which Y is t-butyldimethylsilyl, B is thymine and $R^5$ is 2-ClC$_6$H$_4$ with aqueous triethylamine, followed by concentration, gave a solid, after precipitation with petroleum ether. Analysis of the compound with $^{31}$P-NMR spectroscopy showed a signal at $\delta=7.11$ ppm, with respect to external phosphoric acid.

EXAMPLE III

Reactions of the intermediate formed in Example II with alcohol functions (R$^6$-OH) to obtain a product according to FIG. 5

In the following Table a number of alcohol functions are indicated with which the intermediate with FIG. 4, in which Y is t-butyldimethylsilyl (TBDMS) and $R^5$ is 2-ClC$_6$H$_4$ is able to react.

Figures 8, 9:
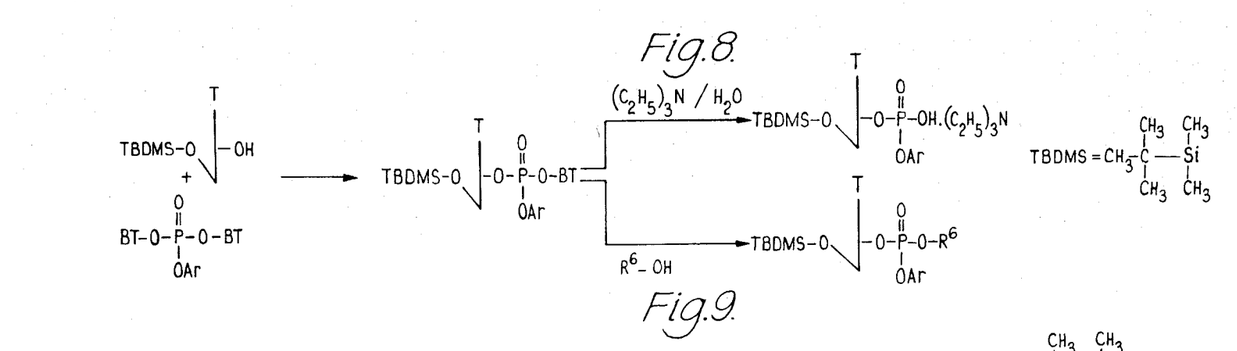

The Table also gives the reaction conditions and the yields. The reaction equation is given in FIG. 9.

TABLE

| | Conditions applied in preparing 3' phosphotriesters (FIG. 5) | | | | |
|---|---|---|---|---|---|
| Exp. No. | Compound 4$^a$ (1.1 mmol) | Alcohol (R$^6$OH) (2.0 mmol) | Tertiary base | Time (h) | Yield (%) |
| 1. | B = T | R$^6$ = —CH$_2$CH$_2$CN | pyridine$^b$ | 3.5 | 95 |
| 2. | B = C$^{An}$ | R$^6$ = —CH$_2$CBr$_3$ | pyridine$^b$ | 3.5 | 75 |
| 3. | B = G$^{DPA}$ | R$^6$ = —CH$_2$CBr$_3$ | pyridine$^b$ | 3.5 | 77 |
| 4. | B = A$^{Bz}$ | R$^6$ = —CH$_2$CBr$_3$ | pyridine$^b$ | 3.6 | 78 |
| 5. | B = T | R$^6$ = 4-nitrophenylethyl | N—methyl-$^c$ imidazole | 1.0 | 88 |
| 6. | B = T | R$^6$ = 5-chloro-8-quinolyl | N—methyl-$^c$ imidazole | 1.0 | 64 |

$^a$Y = t-butyldimethylsilyl (TBDMS).
$^b$To a solution of 4 in THF (5 ml), dry pyridine (2 ml) was added.
$^c$To a solution of 4 in THF (5 ml.) dry N—methylimidazole (4 mmol) was added.

It appears that most alcohol functions that are normally used for the preparation of valuable d-nucleoside 3'-phosphotriester compounds with FIG. 5 can easily be phosphorylated, particularly in the presence of tertiary bases such as pyridine or N-methylimidazole. N-methylimidazole appears to increase the phosphorylation rate about four times more than pyridine does.

EXAMPLE IV

Preparation of dimer or the dinucleotide TpT

Figure 10:
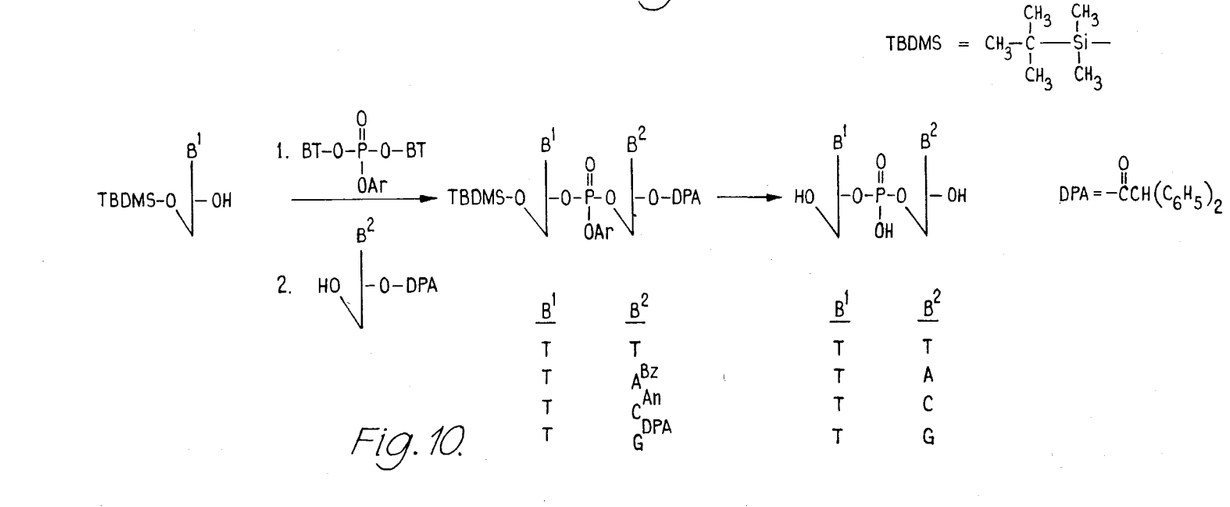

To a stirred solution of phosphotriester intermediary having FIG. 4, in which B is thymine, Y is t-butyldimethylsilyl and $R^5$ is 2-ClC$_6$H$_4$, obtained by treatment of 1.0 mmol 5'-t-butyldimethylsilylthymidine with 1.1 mmol 2-chlorophenylphosphorodi-1-hydroxybenzotriazolidate under conditions as in Example II, there was added 1.0 mmol 3'-O-diphenylacetylthymidine. After 15 minutes 4 mmol N-methylimidazole was added and the reaction mixture was held at 20° C. After 45 minutes TLC-analysis showed that the reaction was complete. After processing and purification of the crude product by means of short column chromatography (see B. J. Hunt and W. Rigby, Chem. Ind.1868 (1967)) 0.93 mmol of the fully protected dimer TpT was obtained. The dimers ApT, CpT, GpT were obtained in an analogous way in yields of about 80%. The reaction equation is given in FIG. 10.

Removal of all protective groups in the dimers by means of oximate treatment, followed by treatment with fluoride ion and finally aqueous ammonia, as described in "Nucleic Acids Res.", 8, 2039 (1980) by J. B. Chattapadhyaya and C. B. Reese, "J.Am.Chem.Soc." 97, 7332 (1975), S. A. Narang c.s. and Recl.Trav.Chim. Pays-Bas, 98, 53 (1979) J. F. M. de Rooij c.s., respectively, provided the corresponding unprotected dimers, which contained only 3'-5'-phosphodiester compounds, which was confirmed by means of $^{31}$P-NMR as well as HPLC-analysis in combination with an enzymatic decomposition procedure in which the enzymes snake poison and spleen phosphodiesterase were used.

EXAMPLE V

Preparation of partially protected dinucleotides with a free 5'-OH group $^{HO}C^{An}pG^{DPA}_{Lev}$, $^{HO}A^{Bz}pT_{Lev}$ and $^{HO}TpT_{Lev}$ 5'-O-t-butyldimethylsilyl-N(4)-anisoyldeoxycytidine($^{TBDMSO}C_{OH^{An}}$) is reacted with 10% molar excess of 2-chlorophenylphosphorodi-1-hydroxy benzotriazolidate and subsequently with 3'-O-levulinoyl-N(2)diphenylacetyldeoxyguanosine ($^{HO}G_{Lev}^{DPA}$) as described in Example IV. Thereafter the 5'-O-t-butyldimethylsilyl group was removed selectively with 5 equivalents p-toluene sulphonic acid in water/acetonitrile (15:85). After processing and purifying under conditions as mentioned in Example IV, pure was obtained.

Figures 11, 12:
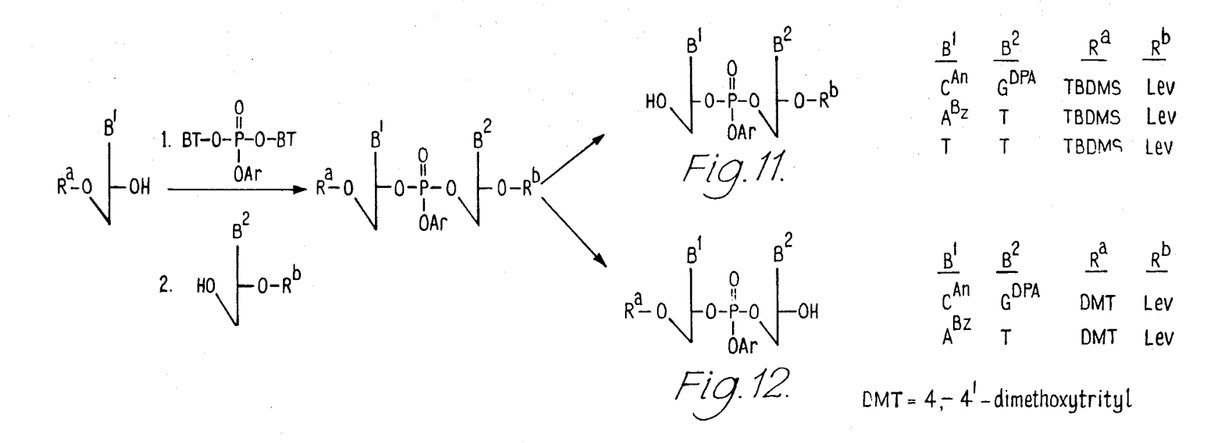

Analogously, the dimer were obtained. The reaction equation is given in FIG. 11.

EXAMPLE VI

Preparation of the partially protected dinucleotides with a free 3'-OH group

In an analogous way as described in Example V, 5'-O-dimethoxytrityl- N(4)-anisoyl deoxycytidine and 3'-O-levulinoyl-N(2)-diphenylacetyl deoxyguanosine were linked by a 3'-5' phosphotriester bridge.

After treatment with hydrazine hydrate (J. H. van Boom and P. M. J. Burgers, Tetrahedron Letters 1976, 4875–4878), in which the levulinoyl group was selectively removed, processing and purification, was isolated in the pure state. In the same way $^{DMT}A^{Bz}_pT_{OH}$ was obtained in a good yield. The reaction equation is given in FIG. 12.

EXAMPLE VII

Figure 13:
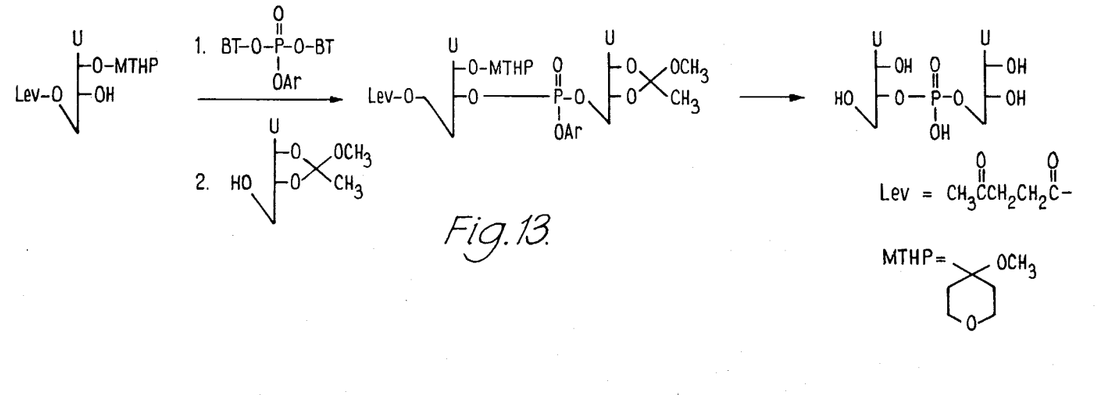

Preparation of UpU 1 mmol 5'-O-levulinoyl-2'-O-(4-methoxytetrahydropyranyl)uridine was reacted with 1.1 mmol 2-chlorophenylphosphorodi-1-hydroxybenzotrazolidate and 1.0 mmol 2',3'-O-methoxymethylene-uridine under conditions as applied in the synthesis of d-nucleoside according to Example IV, except that also 4 mmol pyridine were added. After processing and purification 0.82 mmol UpU were obtained. The reaction equation is given in FIG. 13.

EXAMPLE VIII

Preparation of the oligonucleotide
$^{HO}CpGpApTpCpGpApT_{OH}$ via synthesis on a solid carrier by attaching monomers and elongation from the 3'-position In a suitable vessel, provided with a glass filter, and under inert conditions a solution of 2-chlorophenyl-phosphorodi-1-hydroxy benzotriazolidate in THF, as obtained under the conditions mentioned in Example I, was reacted in a 100% excess with the free hydroxyl group of a functionalised carrier, consisting in this example of a mixture of 3'-hydroxy, 2'-O-acetyl and 2'-hydroxy, 3'-O-acetyl uridine which by means of a 5'-phosphate ester is bound to a spacer, which in its turn is bound covalently to a carrier.

After a reaction time of 20 min, the excess reactant was removed by bringing the reaction vessel at a slight overpressure with an inert gas. Subsequently an excess of 3'-O-levulinoyl-N(4)-anisoyl deoxycytidine ($^{HO}C_{Lev}^{An}$), dissolved in pyridine, and N-methylimidazole were added and the reaction mixture was shaken for 1 hour. After filtration the solid carrier was washed with pyridine, chloroform and pyridine, after which the levulinoyl group was removed with hydrazine hydrate (J. H. van Boom and P. M. J. Burgers, Tetrahedron Letters 1976, 4875–4878) and the washing procedure was repeated.

This tri-step cycle was repeated 7 times with, successively:

3'-O-levulinoyl, N(2)-diphenylacetyl deoxyguanosine ($^{HO}G_{Lev}^{DPA}$),

3'-O-levulinoyl, N(6)-benzoyl deoxyadenosine ($^{HO}A_{Lev}^{Bz}$),

3'-O-levulinoyl, deoxythymidine ($^{HO}T_{Lev}$), again with $^{HO}C_{Lev}^{An}$, again with $^{HO}G_{Lev}^{DPA}$, again with $^{HO}A_{Lev}^{Bz}$ and again with $^{HO}T_{Lev}$ as protected nucleosides.

The last cycle was not followed by removal of the levulinoyl group but by treatment of the solid carrier with oximate and aqueous ammonia, analogously to the manner as indicated in Example IV.

Figure 14:
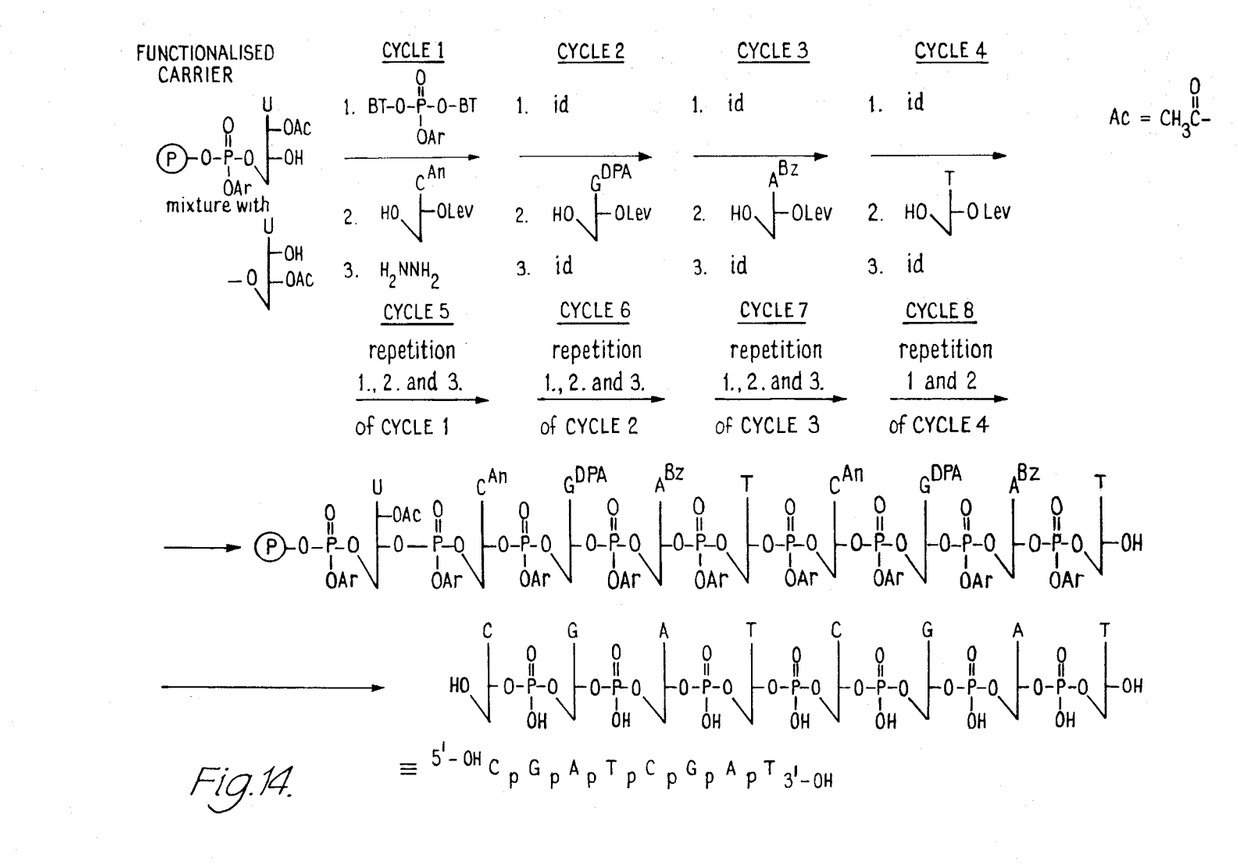

Subsequently the filtrate was purified by means of a gel filtration and the fractions containing the desired product, $^{5'-OH}CpG_pA_pTpCpGpApT_{3'-OH}$ were lyophilised. "Wandering spot analysis" (Determination of Sequences in RNA", G. G. Brownlee, North Holland, Amsterdam 1972) confirmed the sequence of this DNA-fragment. The reactions are shown in FIG. 14.

EXAMPLE IX

Preparation of the oligonucleotide
$^{HO}CpGpApTpCpGpApT_{OH}$ via synthesis on a solid carrier by attaching dimers and elongation from the 3'-position In the way as described in Example VIII the dimer (prepared as described in Example V) was linked to a functionalised carrier. Subsequently the sequence was completed by linking together in 3 cycles, 1, 2 and 3, respectively, and again $^{HO}A^{Bz}pT_{Lev}$ via phosphotriester bridges.

Figure 15:
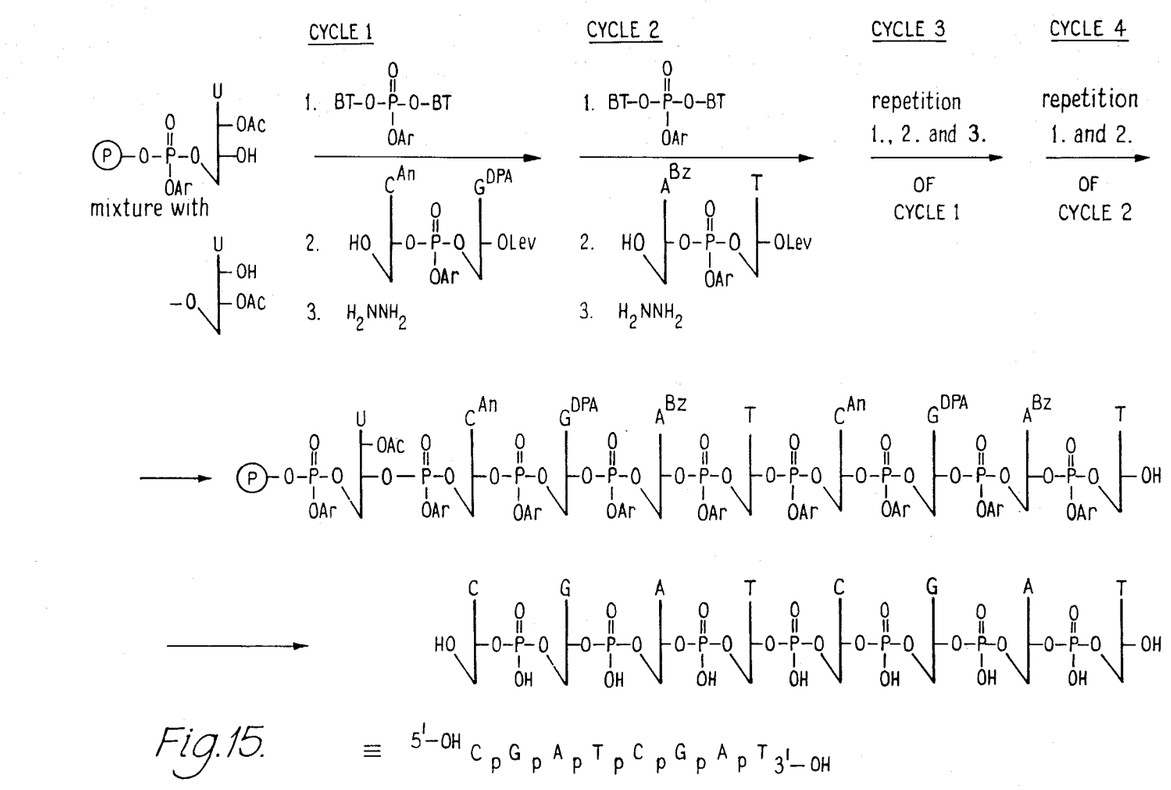

After decoupling of the carrier and purification the "Wandering Spot Analysis" showed that the product obtained was identical with the product from Example VIII. The reactions are shown in FIG. 15.

EXAMPLE X

Preparation of the oligonucleotide
$^{HO}CpGpApTpCpGpApT_{OH}$ via synthesis on a solid carrier by attaching dimers to the 5'-position.

After the reaction of the dimer $^{DMT}A^{Bz}pT_{OH}$ with an equivalent amount of 2-chlorophenylphosphorodi-1-hydroxy-benzotriazolidate as described in Example II, a fourfold molar excess of the intermediate thus formed was added to a functionalised solid carrier. Subsequently N-methylimidazole and pyridine were added, followed by shaking for 1 hour, filtration and washing with pyridine, chloroform and pyridine. Thereafter the DMT group was removed with acid (J. Stawinski, T. Hozumi, S. A. Narang, C. P. Bahland R. Whu, Nucleic Acids Research 4, 353 (1977)).

This cycle was successively repeated three times with the freshly prepared intermediates from $$^{DMT}C^{An}pG^{DPA}_{OH}, \; ^{DMT}A^{Bz}_pT_{OH}$$

and again $$^{DMT}C^{An}pG^{DPA}_{OH},$$

on the understanding that after the last cycle the DMT group was not removed.

The solid carrier, to which the fully protected oligonucleotide had been attached, was first treated with oximate to remove the 2-chlorophenyl groups, then with ammonia to remove the basic labile groups (An, Bz and DPA) and also to selectively break the bond with the functionalised carrier. Subsequently the remaining acidlabile DMT group was removed with aqueous acetic acid.

Figure 16:
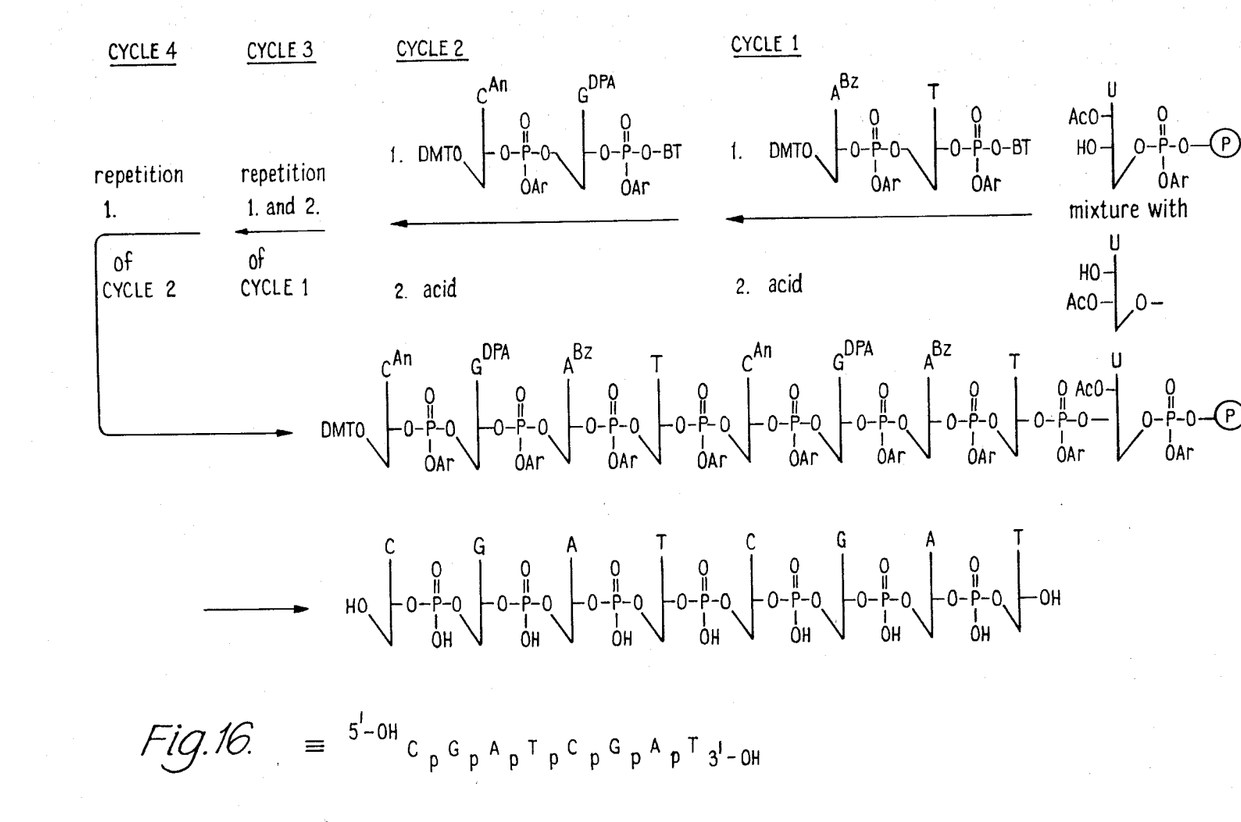

After purification and analysis it was confirmed that the product obtained was identical with the product from Example VI, viz. $5'$-$^{OH}$CpGpApTpCpGpApT$_{3'}$-OH. The reactions are shown in FIG. 16.

I claim:

1. Phosphoric acid derivatives having the formula in which $R^1$, $R^2$, $R^3$ and $R^4$ are alkyl groups having 1–4 C-atoms and/or hydrogen and in which Z is $OR^5$ in which $R^5$ is alkyl or aryl or Z is a primary or secondary amino group.

2. Phosphoric acid derivatives according to claim 1, characterized in that $R^1=R^2=R^3=R^4$ is hydrogen and Z is a morpholino group or an $OR^5$ group in which $R^5$ is a 2-halophenyl- a 4-halophenyl- or a 2-halo-4-alkylphenyl group.

* * * * *